(12) United States Patent
Crawford et al.

(10) Patent No.: US 10,022,155 B1
(45) Date of Patent: Jul. 17, 2018

(54) DYNAMIC LUMBAR SPINE STABILIZATION DEVICE AND METHODS

(71) Applicants: Neil Robert Crawford, Tempe, AZ (US); Phillip Matthew Reyes, Mesa, AZ (US); Nicholas Theodore, Paradise Valley, AZ (US)

(72) Inventors: Neil Robert Crawford, Tempe, AZ (US); Phillip Matthew Reyes, Mesa, AZ (US); Nicholas Theodore, Paradise Valley, AZ (US)

( * ) Notice: Subject to any disclaimer, the term of this patent is extended or adjusted under 35 U.S.C. 154(b) by 258 days.

(21) Appl. No.: 14/938,698

(22) Filed: Nov. 11, 2015

(51) Int. Cl.
*A61B 17/70* (2006.01)
*A61F 2/44* (2006.01)
*A61F 2/30* (2006.01)

(52) U.S. Cl.
CPC ...... *A61B 17/7025* (2013.01); *A61B 17/7011* (2013.01); *A61B 17/7032* (2013.01); *A61B 17/7043* (2013.01); *A61B 17/7044* (2013.01); *A61F 2/44* (2013.01); *A61F 2/442* (2013.01); *A61F 2002/30932* (2013.01); *A61F 2002/449* (2013.01); *A61F 2002/4415* (2013.01)

(58) Field of Classification Search
CPC ............ A61B 17/7025; A61B 17/7019; A61B 17/7032
See application file for complete search history.

(56) References Cited

U.S. PATENT DOCUMENTS

| | | | | |
|---|---|---|---|---|
| 5,672,175 A | * | 9/1997 | Martin | A61B 17/025 606/105 |
| 5,810,815 A | * | 9/1998 | Morales | A61B 17/7053 606/250 |
| 2011/0040331 A1 | * | 2/2011 | Fernandez | A61B 17/701 606/264 |

* cited by examiner

*Primary Examiner* — Christian Sevilla
(74) *Attorney, Agent, or Firm* — Booth Udall Fuller, PLC

(57) ABSTRACT

Dynamic lumbar spine stabilization device implementations and methods are disclosed, which allow for dynamic fixation of both anterior and posterior vertebral columns simultaneously through the articulation of pairs of curved, overlapping rails for partial flexion and extension or up to full normal flexion and extension while stabilizing at least two vertebrae of the lumbar spine.

19 Claims, 5 Drawing Sheets

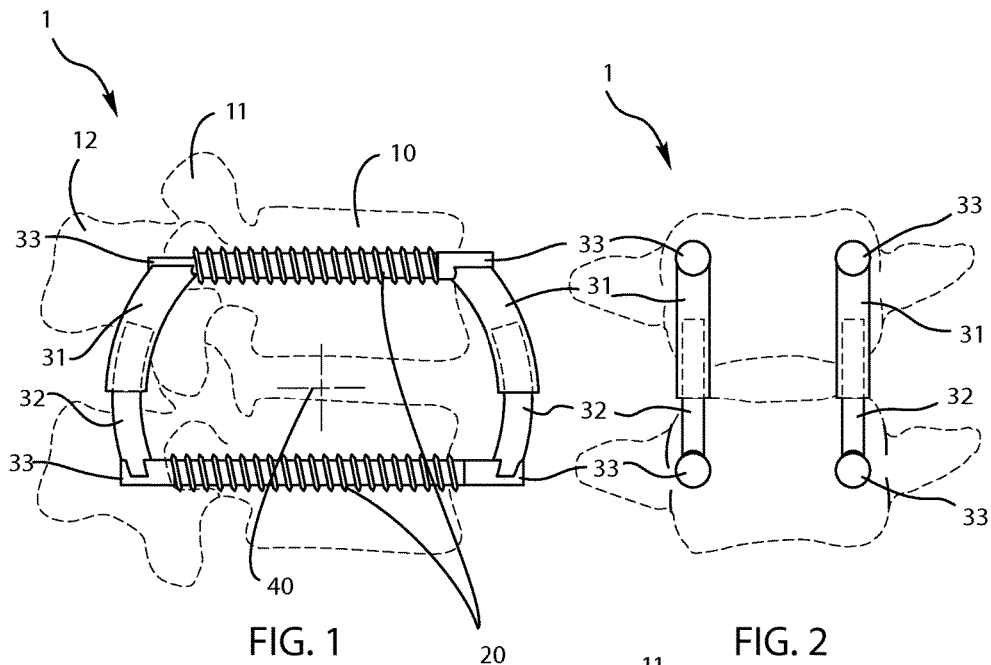
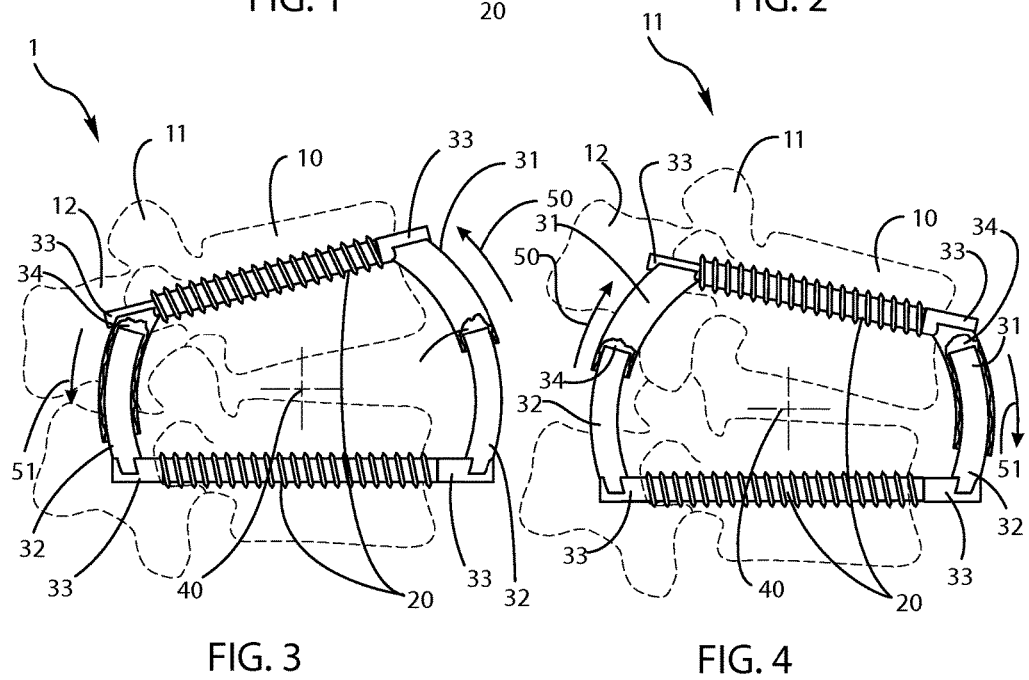

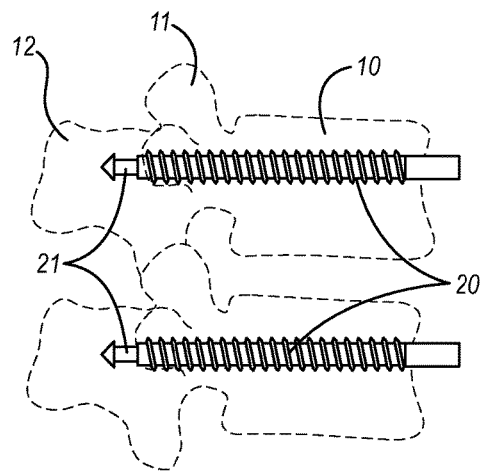
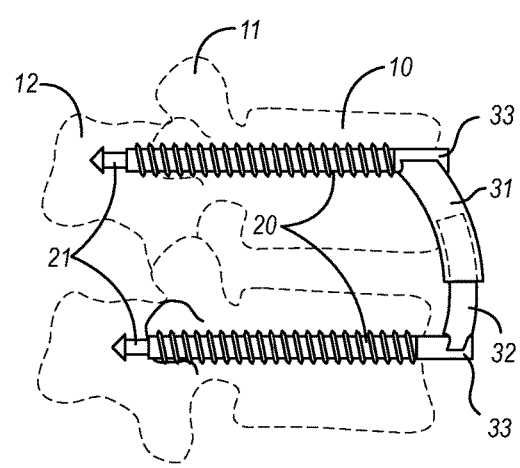
FIG. 5A  FIG. 5B
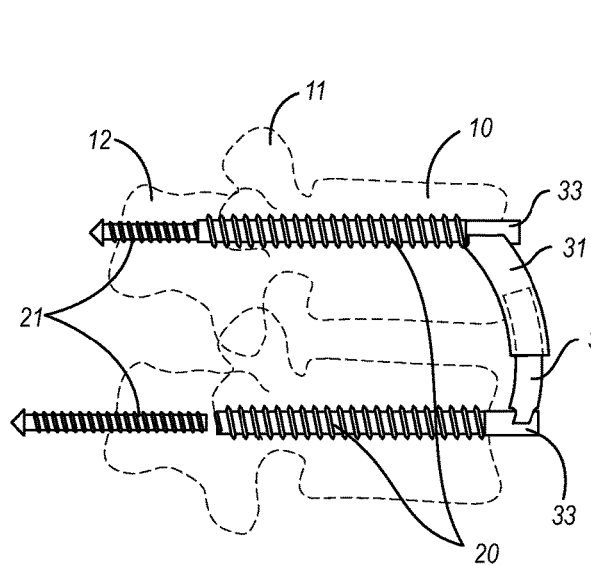
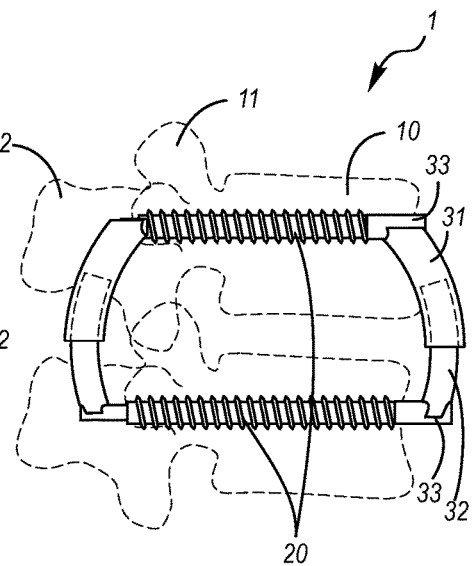
FIG. 5C  FIG. 5D

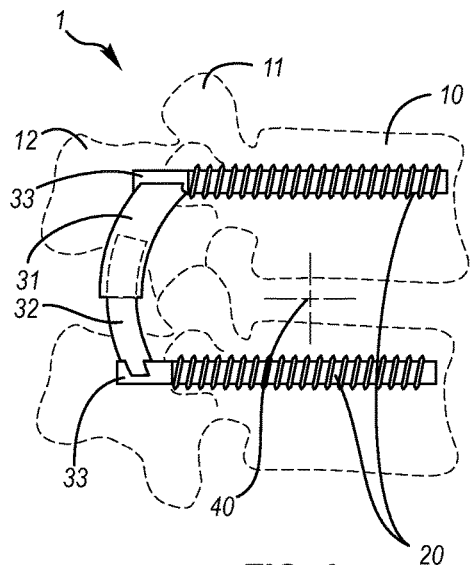
FIG. 6
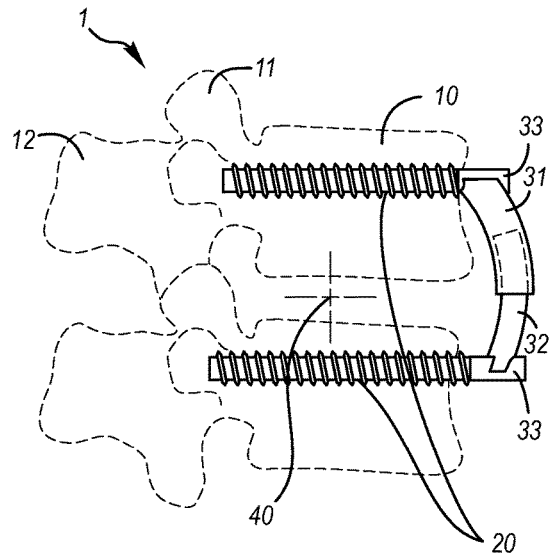
FIG. 7
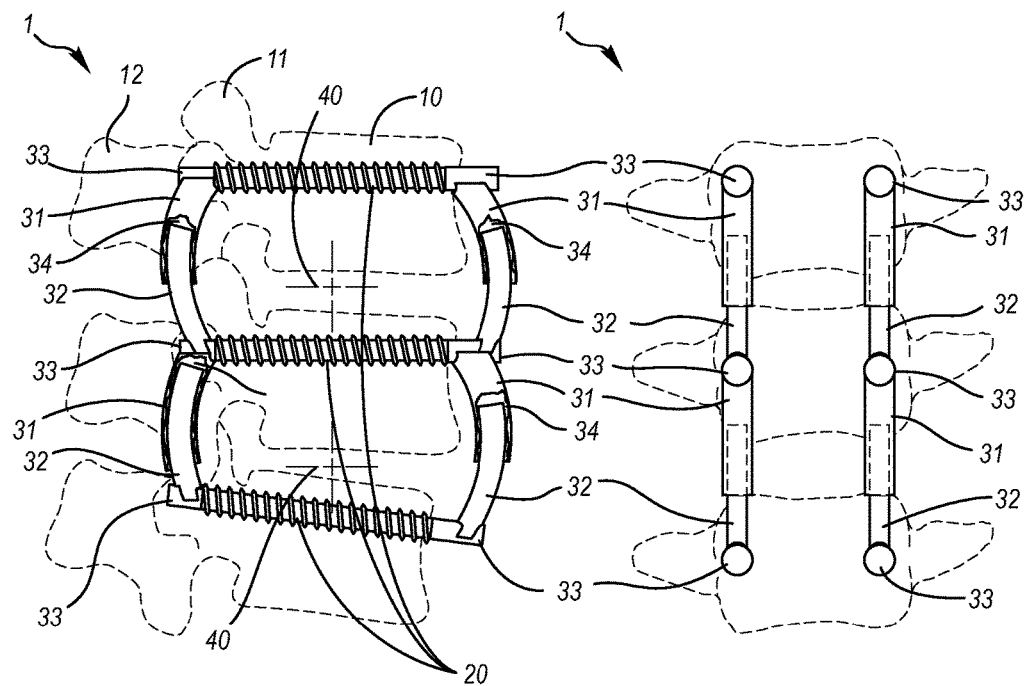
FIG. 8A
FIG. 8B

DYNAMIC LUMBAR SPINE STABILIZATION DEVICE AND METHODS

TECHNICAL FIELD

This document relates to dynamic lumbar spine stabilization device and methods that allow for dynamic fixation of both anterior and posterior vertebral columns simultaneously through the articulation of pairs of curved, overlapping rails for partial flexion and extension or up to full normal flexion and extension while stabilizing at least two vertebrae of the lumbar spine.

BACKGROUND

The lumbar spine allows primarily flexion and extension, while allowing little axial rotation or lateral bending. Dynamic fixation allowing the patient to make natural adjustments to flexion and extension would allow a patient to maintain good sagittal balance. Conversely, fusion at lumbar levels can lead to problems with sagittal balance and degeneration of adjacent levels that are trying to compensate, especially if the index level is fused in the wrong sagittal balance. Maintenance of sagittal balance and prevention of adjacent level degeneration are advantages that proponents of lumbar dynamic fixation cite. The facet joints in the lumbar spine are oriented vertically, blocking anteroposterior translation, limiting axial rotation, and forcing a particular axis of rotation during flexion and extension that is fairly well focused in the posterior two-thirds of the disc. As such, a device allowing only focused flexion and extension while disallowing all other motions (lateral bending, axial rotation, and translation in any direction) would be an ideal lumbar dynamic device.

Current methods of dynamic stabilization in the spine include artificial discs inserted from an anterior or anterolateral approach to restore the function of the natural disc, e.g., Maverick (Medtronic Inc.); ProDisc (DePuy Synthes); Charité (DePuy Synthes), and posterior dynamic stabilization, such as pedicle-screw-based articulating or bending systems, for restoring the function of the facet joints, e.g., Dynesys (Zimmer Spine) and Acadia (Globus Medical). Since degeneration often affects both anterior and posterior columns simultaneously, it would be desirable to dynamically stabilize the spine in both the anterior and posterior columns. However, it is challenging to design anterior and posterior devices that work together to restore the function of the natural disc and facet joints simultaneously.

SUMMARY

Aspects of this document relate to dynamic lumbar spine stabilization device and methods for restoring stability to the lumbar spine after the lumbar spine has become destabilized because of injury, deformity, degeneration, surgical intervention or any other cause. The dynamic lumbar spine stabilization device and methods allow for dynamic fixation of both anterior and posterior vertebral columns simultaneously for partial flexion and extension or up to full normal flexion and extension of the lumbar spine while disallowing other motions. The dynamic lumbar spine stabilization device and methods serve as very good stabilizers in case of high grade spondylolisthesis and/or deformity correction.

The dynamic lumbar spine stabilization device and methods offer several advantages over existing spine stabilization systems. They are (1) stabilization of both anterior and posterior columns synchronously through a continuous attachment, (2) effective replacement of the function of both the disc and facets with one piece of hardware, (3) precise flexion and extension while remaining extremely stable against other loading modes especially compared to alternatives such as artificial discs, (4) lack of requiring removal of the native disc to function properly, thus allowing a less extensive operation, and (5) easy revision to achieve fusion if necessary, in case of a subsequent failure.

These aspects may comprise, and implementations may include, one or more or all of the components and steps set forth in the appended CLAIMS.

In first aspect, a dynamic lumbar spine stabilization device is disclosed, which allows dynamic fixation of both anterior and posterior vertebral columns simultaneously by facilitating partial flexion and extension or up to full normal flexion and extension while stabilizing at least one upper vertebra and at least one lower vertebra of the lumbar spine, wherein the at least one upper vertebra and at least one lower vertebra are either adjacent or non-adjacent.

The dynamic lumbar spine stabilization device of the first aspect allows free movement in sagittal plane while allowing minimum axial rotation, lateral bending and translation in any direction.

The dynamic lumbar spine stabilization device of the first aspect comprises of at least four through-shafts, a first through-shaft extending into a right side of the at least one upper vertebra at least up to a location within the vertebra suitable for insertion of pedicle screws, a second through-shaft extending into a left side of the at least one upper vertebra at least up to a location within the vertebra suitable for insertion of pedicle screws, a third through-shaft extending into a right side of the at least one lower vertebra at least up to a location within the vertebra suitable for insertion of pedicle screws, a fourth through-shaft extending into a left side of the at least one lower vertebra at least up to a location within the vertebra suitable for insertion of pedicle screws.

The dynamic lumbar spine stabilization device of the first aspect also comprises at least two curved rail members, each curved rail member comprising a curved sleeve and a corresponding curved rail moveable within the curved sleeve, the at least two curved rail members coupled to the at least four through-shafts on one of an anterior face, a posterior face, and both anterior and posterior faces of the at least one upper vertebra and the at least one lower vertebra.

In second aspect, a modified dynamic lumbar spine stabilization device is disclosed, which not only allows dynamic fixation of both anterior and posterior vertebral columns simultaneously by facilitating partial flexion and extension or up to full normal flexion and extension but also provides additional support against compression while stabilizing at least one upper vertebra and at least one lower vertebra of the lumbar spine, wherein the at least one upper vertebra and the at least one lower vertebra of the lumbar spine are adjacent. This modified device also allows implantation from a direct lateral surgical approach for the anterior elements of the device instead of requiring an anterior procedure. The direct lateral approach may be more suitable for certain patients.

The modified dynamic lumbar spine stabilization device of the second aspect comprises at least four through-shafts, a first through-shaft extending into a right side of the at least one upper vertebra at least up to a location within the vertebra suitable for insertion of pedicle screws, a second through-shaft extending into a left side of the at least one upper vertebra at least up to a location within the vertebra suitable for insertion of pedicle screws, a third through-shaft extending into a right side of the at least one lower vertebra at least up to a location within the vertebra suitable for insertion of pedicle screws, and a fourth through-shaft extending into a left side of the at least one lower vertebra at least up to a location within the vertebra suitable for insertion of pedicle screws, or at least four pedicle screws, a first pedicle screw inserted into a right side of the at least one upper vertebra, a second pedicle screw inserted into a left side of the at least one upper vertebra, a third pedicle screw inserted into a right side of the at least one lower vertebra, and a fourth pedicle screw inserted into a left side of the at least one lower vertebra.

The modified dynamic lumbar spine stabilization device of the second aspect also comprises at least two curved rail members, each curved rail member comprising a curved sleeve and a corresponding curved rail moveable within the curved sleeve, the at least two curved rail members comprising a first and a second curved rail members, the first curved rail member coupled to the first and the third through-shafts, or the first and the third pedicle screws, on a posterior face of the at least one upper vertebra and the at least one lower vertebra of the lumbar spine, and the second curved rail member coupled to the second and the fourth through-shafts, or the second and the fourth pedicle screws on a posterior face of the at least one upper vertebra and the at least one lower vertebra of the lumbar spine.

The modified dynamic lumbar spine stabilization device of the second aspect further comprises of at least one interbody component placed in intervertebral disc space of the at least one upper vertebra and the at least one lower vertebra for providing additional support against compression, upper half of the at least one interbody component rigidly interconnected to the first and the second through-shafts, or the first and the second pedicle screws and to upper halves of the first and the second curved rail members, lower half of the at least one interbody component rigidly interconnected to the third and the fourth through-shafts, or the first and the fourth pedicle screws and to lower halves of the first and the second curved rail members, the upper and the lower halves of the at least one interbody component share a common axis of rotation with the at least two curved rail members.

Particular implementations of the first and the second aspects may include one or more or all of the following.

The first and the second through-shafts and the third and the fourth through-shafts may extend all the way through the at least one upper vertebra and the at least one lower vertebra, respectively, from an anterior face to a posterior face.

The at least two curved rail members may comprise of first, second, third, and fourth curved rail members, the first curved rail member coupled to the first and the third through-shafts on the posterior face, the second curved rail member coupled to the second and the fourth through-shafts on the posterior face, the third curved rail member coupled to the first and the third through-shafts on the anterior face, and the fourth curved rail member coupled to the second and the fourth through-shafts on the anterior face.

The curved sleeve and the corresponding curved rail moveable within the curved sleeve of each of the at least two curved rail members are curved in a circular path with a path of curvature oriented in a sagittal plane, and the curved sleeve and the corresponding curved rail moveable within the curved sleeve may extend all the way through a space between the at least one upper vertebra and the at least one lower vertebra or extend partially through a space between the at least one upper vertebra and the at least one lower vertebra.

The at least four through-shafts may be selected from the group consisting of solid screws, non-threaded shafts, hollow shafts with cores, or hollow shafts with inserts.

At least one vertically oriented linear sliding mechanism that allows vertical translation may be present at one or more points of connection between each of the at least four through-shafts and each of the at least two curved rail members.

A protective sheath to prevent tissue ingrowth may be present over an area where the curved sleeve and the corresponding curved rail moveable within the curved sleeve of each of the at least two curved rail members slide over each other.

The at least two curved rail members may be coupled to the at least four through-shafts at one or more places by at least one set screw mechanism to allow a surgeon to adjust anteroposterior position of the curved sleeve and the corresponding curved rail moveable within the curved sleeve of each of the two curved rail members in situ.

Interconnecting mechanisms may be present between the at least two curved rail members on left and right side of the at least one upper vertebra and the at least one lower vertebra on one of an anterior face or a posterior face or both anterior and posterior faces to provide additional device rigidity and resistance to lateral bending and axial rotation.

To prevent vertical migration of the at least four through-shafts through the vertebral bodies of the at least one upper vertebra and the at least one lower vertebra in conditions such as osteoporosis, the horizontal surface area covered by the at least four through-shafts may be increased by wings that are deployed laterally after the at least four through-shafts have been placed, or components that grip the at least one upper vertebra and the at least one lower vertebra may be added in regions of stronger cortical bone A low-wear biomaterial flange or coating may be placed to create metal-on-low-wear biomaterial interface between the curved sleeve and the corresponding curved rail moveable within the curved sleeve of each of the at least two curved rail members. The low-wear biomaterial may be selected from a group consisting of ceramic, polycarbonate, polyethylene, polyether ether ketone, or any low-wear biocompatible polymer.

Non-metallic stops such as elastic bumpers or dashpots or both bumpers and dashpots may be added to ends of the curved sleeve or the corresponding curved rail moveable within the curved sleeve of each of the at least two curved rail members to prevent stiff abrupt stops when the end of the corresponding curved rail moveable within the curved sleeve collides with the end of the curved sleeve, thereby controlling magnitude and speed of rotation of the at least two curved rail members.

Springs may be incorporated to ends of the curved sleeve or the corresponding curved rail moveable within the curved sleeve of each of the at least two curved rail members to allow controlling position of the joint to a desired neutral position and to provide elastic resistance to motion away from the desired neutral position.

The curved sleeve and the corresponding curved rail moveable within the curved sleeve of each of the at least two curved rail members may have a non-circular cross-section.

The at least one interbody component may be selected from the group consisting of a ball and socket, a cylindrical hinge with axis perpendicular to the sagittal plane, a flexible and pliable material with mechanical properties of soft rubber, or any other biocompatible elastomeric material that allows free flexion and extension.

Plates and bone screws, or plates and cement, or plates and bone screws and cement, or keels or spikes may be used to secure the at least one interbody component to vertebral bodies of the at least one upper vertebra and the at least one lower vertebra. The plates may comprise of attachment plates interconnecting the at least one interbody component and the at least two curved rail members to facilitate the at least one interbody component and the at least two curved rail members sharing a desired common axis of rotation. The plates may further comprise of left, right or bilateral anterolateral plate components extending from the at least one interbody component to secure the at least one interbody component to the vertebral bodies of the at least one upper vertebra and the at least one lower vertebra.

The first and the second through-shafts and the third and the fourth through-shafts may extend all the way through the at least one upper vertebra and the at least one lower vertebra, respectively, from an anterior face to a posterior face. The at least two curved rail members may comprise of first, second, third, and fourth curved rail members, the first curved rail member coupled to the first and the third through-shafts on the posterior face, the second curved rail member coupled to the second and the fourth through-shafts on the posterior face, the third curved rail member coupled to the first and the third through-shafts on the anterior face, and the fourth curved rail member coupled to the second and the fourth through-shafts on the anterior face. The upper half of the at least one interbody component is rigidly interconnected to the first and the second through-shafts and upper halves of the first and the second curved rail members and the lower half of the at least one interbody component rigidly interconnected to the third and the fourth through-shafts and to lower halves of the first and the second curved rail members, or the upper half of the at least one interbody component rigidly interconnected to the first and the second through-shafts and upper halves of the third and the fourth curved rail members and the lower half of the at least one interbody component rigidly interconnected to the third and the fourth through-shafts and to lower halves of the third and the fourth curved rail members. The first, the second, the third and the fourth through-shafts, the first, the second, the third and the fourth curved rail members, the at least one interbody component, and other components of the device are surgically implanted into a subject by both anterior exposure and posterior exposure.

In third aspect, a method for implanting the dynamic lumbar spine stabilization device of first aspect is disclosed. The method comprises of surgically implanting the dynamic lumbar spine stabilization device of first aspect into a subject by performing at least one of an anterior exposure or a posterior exposure or both anterior and posterior exposures, and using a rigid guide plate or guide jig to ensure that the at least four through-shafts of the dynamic lumbar spine stabilization device follow coordinated trajectories.

In one implementation of the third aspect, the method may be performed using image guidance with or without robotic assistance to pre-plan and execute coordinated trajectories for the at least four through-shafts.

In fourth aspect, a method for implanting the modified dynamic lumbar spine stabilization device of the second aspect into a subject is disclosed. The method comprises implanting the modified dynamic lumbar spine stabilization device of the second aspect surgically into the subject by a posterior exposure and an extreme lateral interbody fusion approach thereby eliminating the need for an anterior exposure. The posterior exposure is used to surgically implant the at least four through-shafts or the at least four pedicle screws, the at least two curved rail members and other components interconnecting the at least four through-shafts or the at least four pedicle screws, the at least two curved rail members, and the at least one interbody component. The extreme lateral interbody fusion approach is used to insert the at least one interbody component, the attachment plates, the left, right, or bilateral anterolateral plate components, and any other components used to secure the at least one interbody component to the at least one upper vertebra and the at least one lower vertebra.

BRIEF DESCRIPTION OF DRAWINGS

Implementations will hereinafter be described in conjunction with the appended DRAWINGS (which are not necessarily to scale), where like designations denote like elements.

FIGS. 1 and 2 are lateral and anterior views, respectively, of a dynamic lumbar spine stabilization device implementation mounted on a lumbar motion segment.

FIGS. 3 and 4 are lateral views of the dynamic lumbar spine stabilization device of FIGS. 1 and 2 while in extension and flexion, respectively.

FIGS. 5A-5D depict stages in possible steps involved in surgical implantation of the dynamic lumbar spine stabilization device implementation of FIGS. 1 and 2. (FIG. 5A) After anterior exposure, through-shafts, which contain cores that provide a sharp distal tip and possibly extend the length of the through-shaft on the distal tip are implanted. (In FIG. 5B) Curved rail members are attached to the through-shafts on anterior face and anterior exposure is closed. (In FIG. 5C) After posterior exposure, cores are removed from through-shafts, leaving attachment points for curved rail members. (FIG. 5D) Curved rail members are mounted to the through-shafts on posterior face.

FIG. 6 is a lateral view of the dynamic lumbar spine stabilization device implementation of FIGS. 1 and 2 where only the posterior half is used. Through-shafts do not extend all the way through the upper or the lower vertebrae.

FIG. 7 is a lateral view of the dynamic lumbar spine stabilization device implementation of FIGS. 1 and 2 where only the anterior half is used. Through-shafts terminate within the vertebrae at the pedicle region.

FIGS. 8A and 8B are lateral and anterior views, respectively, showing how multiple levels may be configured with the dynamic lumbar spine stabilization device implementations. Multiple centers of rotation are defined by placement of curved rail members.

DESCRIPTION

Figure 9:
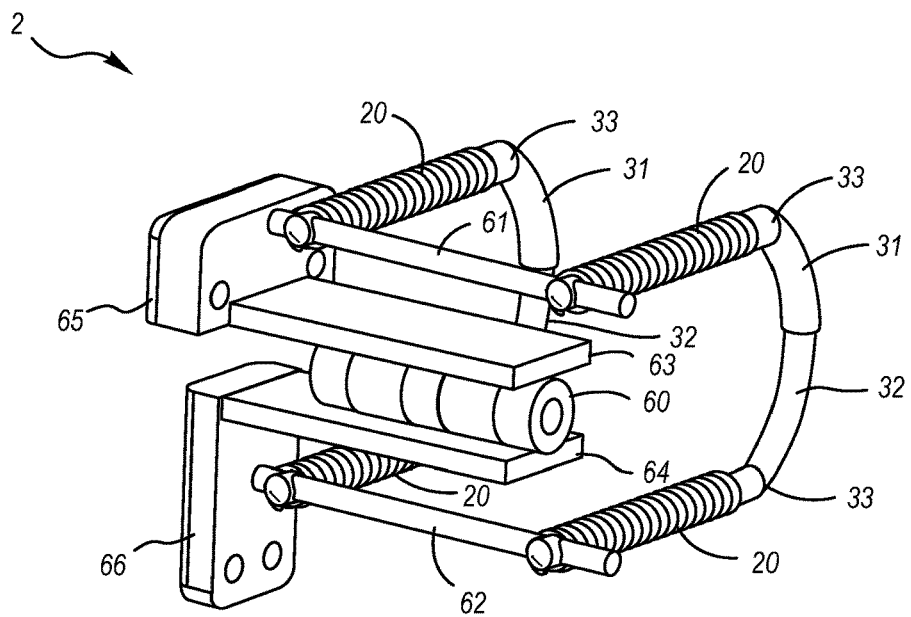
FIG. 9 is a perspective view of another implementation of a dynamic lumbar spine stabilization device. Attachment plates interconnect the interbody hinge and curved rail members.

This document features a surgically implantable dynamic lumbar spine stabilization device implementations that allow partial flexion and extension or up to full normal flexion and extension while stabilizing at least two vertebrae.

There are many features of the dynamic lumbar spine stabilization device and method implementations disclosed herein, of which one, a plurality, or all features or steps may be used in any particular implementation.

In the following description, reference is made to the accompanying DRAWINGS which form a part hereof, and which show by way of illustration possible implementations. It is to be understood that other implementations may be utilized, and structural, as well as procedural, changes may be made without departing from the scope of this document. As a matter of convenience, various components will be described using exemplary materials, sizes, shapes, dimensions, and the like. However, this document is not limited to the stated examples and other configurations are possible and within the teachings of the present disclosure.

There are a variety of dynamic anterior and posterior spine stabilization device implementations that allow partial or up to full normal flexion and extension while stabilizing at least two vertebrae. In one aspect, a dynamic anterior and posterior spine stabilization device may generally include at least four through-shafts that extend partially or all the way through the at least one upper vertebra and at least one lower vertebra, and at least two curved rail members coupled to the at least four through-shafts on one of an anterior face, a posterior face, and both anterior and posterior faces of the at least one upper vertebra and the at least one lower vertebra. Each of the at least two curved rail members comprise of a curved sleeve and a corresponding curved rail moveable within the curved sleeve.

For example, each of the at least two curved rail members may be coupled to the at least four through-shafts by at least one set screw mechanism.

The curvature of the curved sleeve and the corresponding curved rail moveable within the curved sleeve of each of the curved rail members is such that the center of rotation during flexion and extension remains located at the normal position in the sagittal plane. Thus, the curved sleeve and the corresponding curved rail moveable within the curved sleeve may be curved in a circular path, with the path of curvature oriented predominantly in the sagittal plane.

Accordingly, the dynamic lumbar spine stabilization device allows ample sagittal rotation, but generally disallows rotation in other planes or translation in any plane, although considerations for small amounts of motion in other directions are given. To this end for example, the cross-section of the curved sleeve and the corresponding curved rail moveable within the curved sleeve of each of the curved rail members may be a non-circular geometry.

Notwithstanding, turning to FIGS. 1-7 and for the exemplary purposes of this disclosure, dynamic lumbar spine stabilization device 1 is shown. Dynamic lumbar spine stabilization device 1 may include at least two separate components: through-shaft 20 and curved rail member comprising of a curved sleeve 31 and a corresponding curved rail moveable within the curved sleeve 32.

Dynamic lumbar spine stabilization device 1 may be mounted on a lumbar motion segment using four through-shafts 20. Only two through-shafts 20 (upper right and lower right) are visible in lateral view FIG. 1. In anterior view FIG. 2, the four through shafts are not visible as they are positioned in line with and behind the four through shaft extensions 33. Four curved rail members with each comprising of a curved sleeve 31 and a corresponding curved rail moveable within the curved sleeve 32 interconnect the through-shafts of the upper and lower vertebrae. Only two curved rail members (anterior right and posterior right) are visible in lateral view FIG. 1 and only two curved rail members (anterior right and anterior left) are visible in anterior view FIG. 2. The curved sleeve 31 of the anterior right curved rail member is coupled to the upper right through-shaft 20 and the corresponding curved rail moveable within the curved sleeve 32 of the anterior right curved rail member is coupled to the lower right through-shaft. Likewise, the curved sleeve 31 of the posterior right curved rail member is coupled to the upper right through-shaft 20 on anterior face and the corresponding curved rail moveable within the curved sleeve 32 of the anterior right curved rail member is coupled to the lower right through-shaft 20 on anterior face. The anterior and posterior curved rail members have a coordinated center of curvature. During sagittal plane bending (flexion-extension), the axis of rotation 40 is forced to this center of curvature.

In FIG. 3, dynamic lumbar spine stabilization device 1 is shown while under extension. Under extension, the curved sleeve 31 and the corresponding curved rail moveable within the curved sleeve 32 of the posterior right curved rail member completely slide over each other (movement represented by 51) while the curved sleeve and the corresponding curved rail moveable within the curved sleeve of the anterior right curved rail member completely move away from each other (movement represented by 50).

In FIG. 4, dynamic lumbar spine stabilization device 1 is shown while under flexion. Under flexion, the curved sleeve 31 and the corresponding curved rail moveable within the curved sleeve 32 of the anterior right curved rail member completely slide over each other (movement represented by 51) while the curved sleeve and the corresponding curved rail moveable within the curved sleeve of the posterior right curved rail member completely move away from each other (movement represented by 50).

In FIGS. 5A-5D, possible steps for surgical implantation of dynamic lumbar spine stabilization device 1 are disclosed. Dynamic lumbar spine stabilization device 1 includes anteriorly and posteriorly inserted portions that meet to create the final configuration. Surgical implantation of the device requires a two-step surgery—first an anterior exposure (FIGS. 5A and 5B) then a posterior exposure (FIGS. 5C and 5D). The vertebrae that are instrumented may be consecutive (e.g., L4-L5) or interrupted (e.g., L3-L5), although typically consecutive vertebrae would be instrumented.

The anterior exposure (FIG. 5A) is performed to expose the index vertebral bodies 10 to the left and right of midline. After exposing the vertebral body at the appropriate level, 4 holes are drilled (2 per vertebra): each hole extending through the vertebral body 10, then through the pedicle 11, and then through and out the posterior elements 12 of the upper vertebra and the lower vertebra. For e.g., for L4-L5 instrumentation, one hole passes through the left body/pedicle/posterior elements of L4, one hole through the right body/pedicle/posterior elements of L4, one hole through the left body/pedicle/posterior elements of L5, and one hole through the right body/pedicle/posterior elements of L5.

After creating the holes, it may be desirable to mark and maintain the trajectories using guide wires, which could extend distally all the way out through the skin on the patient's back. The four through-shafts 20 (upper right and upper left through-shafts extending through the right and left sides of the upper vertebra, lower right and lower left through-shafts extending through the right and left sides of the lower vertebra) for the implanted device are then attached in each vertebra (FIG. 5A). The through-shafts could be solid screws or non-threaded shafts, or could be hollow with inserts that provide pointed tips and elongate the shaft temporarily so they can be found more easily when posterior exposure is performed. The through-shafts of the envisioned device are screw threaded through-shafts 20 with cores 21 inserted that provide a sharp distal tip and possibly extend the length of the through shaft on the distal tip (FIGS. 5A, 5B and 5C). From the anterior bases of these through-shafts 20, curved sleeve 31 and corresponding curved rail moveable within the curved sleeve 32 of each of the four curved rail members are anchored to form extensions interconnecting the upper and lower vertebrae bilaterally (FIG. 5B). As such, the upper right and lower right through-shafts on anterior face are connected by anterior right curved rail member, and the upper left and lower left through-shafts on anterior face are connected by anterior left curved rail member. After mounting and securing the curved rail members anteriorly, the anterior exposure may be closed (FIG. 5B) and posterior exposure undertaken.

The posterior exposure is performed (FIG. 5C) to expose the posterior elements of the index levels to the left and right of midline. If guide wires were used in the anterior implantation, the surgeon would now seek the distal ends of these guide wires. If temporary elongated attachments or cores 21 to the through-shafts were used, the ends of these elongations would be found and these components would be removed after appropriate surgical exposure (FIG. 5C). Whether or not elongation is used, the surgeon would surgically expose the region where the through-shafts 20 exit posteriorly, which can be predicted from preoperative imaging and planning.

Once the through-shafts have been located, posterior curved rail members with curved sleeve 31 and corresponding curved rail moveable within the curved sleeve 32 are attached to the through-shafts on posterior face thereby making a continuous dynamic fixation construct (FIG. 5D). Similar to the anterior extensions, the posterior extensions are also curved rail members that interconnect the index vertebrae to the left and right of midline. As such, the upper right and lower right through-shafts on posterior face are connected by posterior right curved rail member, and the upper left and lower left through-shafts on posterior face are connected by posterior left curved rail member. It may be necessary to resect some portion of the posterior elements to make it possible to attach the posterior portion of the surgical implant.

It is important that the surgeon be able to appropriately position the hardware to achieve the desired center of rotation. Preoperative planning will be needed to determine the correct radius of curvature of the curved sleeve and the corresponding curved rail moveable within the curved sleeve of each of the curved rail members to position them appropriately. An offset center of rotation could lead to unwanted impingement on the neural elements during flexion-extension or the implant struggling against the native tissues to achieve a coordinated axis of rotation. Mechanisms for adjustment of the hardware could be incorporated into the base of the through-shafts and anterior curved rail members, through-shafts and posterior curved rail members, or both. Adjustments could be made using set screws or set screw mechanisms to allow repositioning in anteroposterior, rostrocaudal, and lateral directions in situ (during surgical placement).

Preoperative or intraoperative planning could be used to identify the correct positioning and size of the hardware. For example, a computed tomography image could be used to identify the exact anteroposterior distances where through-shafts enter and exit the vertebral bodies and posterior elements. The correct radius of curvature of the device could then be selected based on the estimated location of the axis of rotation or based on the axis of rotation at an adjacent intact level. An estimated location could be obtained from images of healthy intact spines or from a calculation or template utilizing curvature of facets and disc shape. Through-shaft screw locations and lengths could be pre-planned so that the device would be inserted in the correct position. Screws could then be inserted using image guidance through optical tracking, as is currently done for other techniques in the same region such as lumbar pedicle screws.

It may be desirable to interconnect the left and the right curved rail members on anterior face and/or the left and the right curved rail members on posterior face rather than to have them be independent, although the dynamic fixation device could be fully functional without interconnection. Interconnecting would improve overall rigidity of the device and provide additional resistance to lateral bending and axial rotation and would ensure true flexion-extension without seizing of the curved sleeve and the corresponding curved rail moveable within the curved sleeve of each of the curved rail members. Interconnection could be performed by lateral cross-linking elements attached anteriorly, posteriorly, or both.

The cross-sections of the curved sleeve and the corresponding curved rail moveable within the curved sleeve could be of any shape. Although feasible, a circular cross-section may be suboptimal since forces that are trying to cause rotation in planes other than the sagittal plane might cause the curved sleeve and the corresponding curved rail moveable within the curved sleeve of each of the curved rail members to "seize" and lock up. Other shapes, such as square, rectangular, or slotted, would probably prevent seizing more effectively.

One possible long-term complication of the implanted hardware could be loosening at the screw-bone interfaces. To prevent such an occurrence, certain steps could be taken. One possibility is to increase the strength of the screw-bone interface by applying a hardware surface (porous coating) into which bone fibers can grow. Bony ingrowth or overgrowth can be enhanced on a cellular level by application of a bone growth promoter such as BMP (bone morphogenetic protein) or application of electrical or magnetic stimulation. Another possibility is to enhance the fixation of the screws using augmentation such as cement around the screw, cement injected through fenestrations in the screw, or hardware features otherwise anchoring the screw, such as drywall anchors. However, such a complication is less likely to occur with the devices described herein since the vertebrae are "captured" between the anterior and posterior anchors.

Another possible long-term complication of the implanted hardware is migration vertically through the vertebral bodies of the through-shafts due to prolonged forces from gravity and activity. This complication might be more likely to occur if the patient's bone is osteoporotic. One way to overcome this problem would be to enhance the horizontal surface area covered by the through-shafts, possibly by "wings" that are deployed laterally after shafts have been placed. Another way to overcome this problem would be to add components that grip the vertebrae in regions of stronger cortical bone. Anteriorly, additional anchors could reach up and/or down from the through-shaft entry sites and be secured to bone in the region near the end-plates. Posteriorly, hooks or other extensions could reach around posterior or lateral bony elements of the spine to serve as additional sites of fixation.

Another possible long-term complication of the implanted hardware is tissue ingrowth into the sliding regions of the curved rails. To prevent tissue ingrowth, it is possible to incorporate a protective sheath or membrane 34 (FIGS. 3 and 4) into the design to cover the sliding regions. Such a membrane could be accordion-like, encompassing the entire assembly, so that portions of the accordion membrane compress or expand as the curved sleeve and the corresponding curved rail moveable within the curved sleeve of each of the curved rail members overlap, or separate membrane pieces could be on the curved sleeve and the corresponding curved rail moveable within the curved sleeve of each of the curved rail members, and the membranes themselves overlap, being tightly enough in apposition to keep tissue out but loose enough to allow sliding. Alternately, it is possible to coat the hardware with a material that chemically prevents overgrowth or to intermittently apply electrical stimulation of an amplitude and frequency that might prevent tissue formation or ablate any newly formed tissue that might have been deposited.

The curved sleeve and the corresponding curved rail moveable within the curved sleeve of each of the curved rail members must slide across each other through numerous daily cycles. Such behavior would be expected to generate wear debris, which may have a negative effect on surrounding tissues and should be minimized. Different material interfaces could be used to minimize wear debris. It may be possible to incorporate a ceramic flange on the female overlapping curved rail to allow metal-on-ceramic interface, which should have good wear debris properties. Or, the flange could be polyethylene or other polymer to enable a metal-on-polymer interface.

It may be desirable if there is only mild instability to omit one half of dynamic lumbar spine stabilization device 1. That is, posterior fixation consisting of four through-shafts 20 and two posterior curved rail members (each curved rail member comprising of curved sleeve 31 and corresponding curved rail moveable within the curved sleeve 32) might be the only device implanted (FIG. 6), in which case the through-shafts would not need to extend all the way through and would terminate in a location typical for pedicle screws. As such in posterior fixation, the posterior right curved rail member interconnects the upper right and lower right through-shafts on posterior face and the posterior left curved rail member interconnects the upper left and lower left through-shafts on posterior face.

Alternately, anterior-only fixation consisting of four through-shafts and two anterior curved rail members (each curved rail member comprising of curved sleeve 31 and corresponding curved rail moveable within the curved sleeve 32, coupled via extensions 33 to the four through-shafts on anterior face) might be the only device implanted (FIG. 7), with through-shafts terminating before breaking out posteriorly. As such in anterior fixation, the anterior right curved rail member interconnects the upper right and lower right through-shafts on anterior face and the anterior left curved rail member interconnects the upper left and lower left through-shafts on anterior face.

The curved sleeve and the corresponding curved rail moveable within the curved sleeve of each of the curved rail members are free to move in flexion and extension, but in other directions, motion is limited by the articulations of the curved rails. One motion that is of concern with regard to durability of the device is repeated vertical compression such as would occur during walking or other daily activities. Such a motion would be expected to occur with greater stiffness than if a natural disc were present because it is a rail-on-rail, metal-on-metal interaction. It may be possible to build in some vertical elasticity (shock absorbers) to help cushion this interaction. Such shock absorbers could be mechanisms built into the interfaces between the curved sleeve and the corresponding curved rail moveable within the curved sleeve of each of the curved rail members (upper, lower, or both), thus allowing vertical mobility with spring-loaded resistance.

In flexion or extension, the end of rotation is encountered when the end of the corresponding curved rail moveable within the curved sleeve collides with end of the curved sleeve. This collision would represent a stiff, abrupt stop to flexion or extension. It is possible to introduce a more flexible stop through selection of the material used for the curved sleeve and the corresponding curved rail moveable within the curved sleeve of each of the curved rail members and/or through usage of non-metallic stops, such as elastic "bumpers" at each end of the curved sleeve and the corresponding curved rail moveable within the curved sleeve of each of the curved rail members. It is also possible to create an interface between overlapping curved rail sections that incorporates a viscous damper (like the dashpot used on some doors to make them close slowly) so that motion does not occur without resistance at the instrumented motion segment. Such a strategy would prevent this motion segment from being the "path of least resistance" to loads applied to the spine, preventing motion from being exaggerated at the index level. Furthermore, it is possible to incorporate a spring mechanism that keeps the device centered at a chosen neutral position of the curved rails, with resistance to motion being slight when the joint is in the neutral position and a restoring force being greater and greater the farther the joint is from the desired neutral position.

For good fit of anterior and posterior portions, it is desirable for the through-shafts to pass through the vertebral body in a controlled trajectory. One way to enable the surgeon to control the trajectory is by the usage of a rigid guide plate or jig, with holes for guiding the position and angle of all four of the through-shafts. The appropriate sized plate would be selected from a set of plates; alternately a guide jig would have mechanisms to adjust the left-right and inferior-superior hole spacing to suit the anatomy. The plate or jig would remain in place temporarily while passing the four through-shafts from anterior to posterior and then would be removed. A second plate or jig for use from the posterior face would confirm and slightly refine trajectories. Another method to enable the surgeon to control the through-shaft trajectories is by image guidance. The desired trajectories would be pre-planned on medical images, and software features would ensure that planned trajectories were coordinated so that the final orientation would optimally suit the positions of the through-shafts and other components. Additionally, a surgical robot that is synchronized with image guidance could be used to hold a guide tube during through-shaft hole preparation to ensure that the through-shafts are actually inserted following the planned trajectories.

It may be desirable to interconnect the curved rail members to a motion-sparing prosthesis or fusion device at adjacent levels, particularly with additional curved rail members at consecutive levels. Considerations could be incorporated into mounting posts to accept multiple curved rail members or curved rail members that have multiple curves (FIGS. 8A and 8B). In FIGS. 8A and 8B, the device comprises of multiple levels that are configured and multiple centers of rotation are defined by placement of curved sleeve and corresponding curved rail moveable within the curved sleeve of each of the curved rail members.

Figure 10:
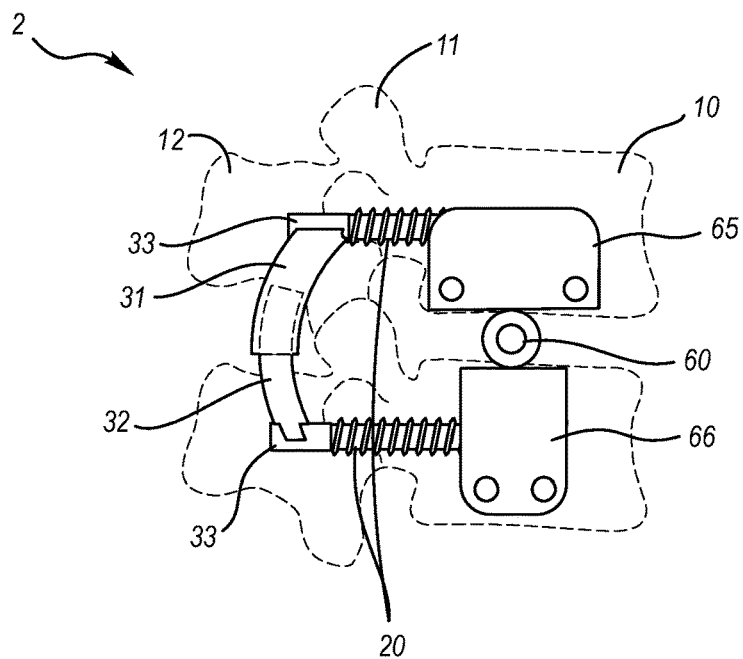
FIG. 10 is lateral view of two vertebrae with the dynamic lumbar spine stabilization device implementation of FIG. 9 mounted on a lumbar motion segment implanted via posterior and extreme lateral fusion approach. Pedicle screw extensions and interbody hinge extensions are interconnected via rigid solid pieces with holes to accept the extensions.

In FIGS. 9-10 and for the exemplary purposes of this disclosure, a modified dynamic lumbar spine stabilization device 2 is shown. Modified dynamic lumbar spine stabilization device 2 may include at least three separate components: through-shaft 20, curved rail member comprising of a curved sleeve 31 and a corresponding curved rail moveable within the curved sleeve 32, and an interbody component.

Interbody components may be rigidly interconnected to the rest of the device and inserted in the disc space after performing discectomy. The advantage of such a piece is that it provides support against compression that would otherwise have to be borne by the curved sleeve and corresponding curved rail moveable within the curved sleeve of each of the curved rail members.

The interbody component inserted in the disc space should be a device that allows free bending, especially in flexion and extension. Such a device could be a ball-and-socket, a cylindrical hinge with axis aligned perpendicular to the sagittal plane, or a flexible, pliable material with mechanical properties of soft rubber. A hinge for example provides for less point contact and therefore would transfer less stress to the hardware. Also a hinge is more easily made "closed" so that it cannot distract. Preventing distraction may confer additional stability to the prosthesis. An elastomeric material in the disc space would not have as rigid or constrained of an interface with the rails as would a hinge or ball-and-socket. This property may or may not be desirable depending on the tolerances of the articulating sections. If a hinge is used, the center of rotation must match the center of rotation dictated by the curved sleeve and the corresponding curved rail moveable within the curved sleeve of each of the curved rail members.

One half of the interbody component is rigidly interconnected to upper halves of curved rail members and upper through-shafts while the other half of the hinge is rigidly interconnected to lower halves of curved rail members and lower through-shafts. If desired, the interbody component could be secured to the vertebral bodies of the motion segment for which it is applied using plates and bone screws and/or cement.

In particular, interbody component 60 may be cylindrical hinge inserted into the intervertebral disc space with its axis aligned perpendicular to the sagittal plane. Attachment plates 61, 62 rigidly interconnect the interbody component and the posterior curved rail members to allow the interbody component and the curved sleeve and the corresponding curved rail moveable within the curved sleeve of each of the posterior curved rail members to function synchronously of the motion segment (FIG. 9). In such an implementation, anterior curved rail members are not present. Such a device is inserted through an extreme lateral (XLIF) fusion approach and a posterior approach instead of anterior and posterior approaches as depicted in FIGS. 5A-5D. Since it would probably be infeasible to apply anterior curved rail members to vertebrae via an XLIF approach, it is logical that the modified device would be without anterior curved rail members.

Pedicle screws 20 may be inserted into right and left pedicles of the upper vertebra, and also in right and left pedicles of the lower vertebra. Interbody component 60 and left, right or bilateral anterolateral plate components 63, 64 and/or other additional components may be placed in the intervertebral disc space and adjacent vertebral bodies. The interbody component 60 may be rigidly interconnected with posterior curved rail members via attachment plates so that the interbody component and the curved sleeve and the corresponding curved rail moveable within the curved sleeve of each of the posterior curved rail members function synchronously. As shown in FIG. 9, bilateral anterolateral plate components 63, 64 extending from the interbody component 60—one plate from each half of the hinge—could be rigidly interconnected with the pedicle screws 20 if properly aligned, the screws being used to secure the interbody component to vertebral bodies of the upper and the lower vertebrae. Additionally, screws into the bone could further anchor the bilateral anterolateral plate components 63, 64.

Several variations of the bilateral anterolateral plate components extending from the interbody component 60 may be used. The extension from pedicle screws 20 and an extension from the interbody component 60 may be temporarily locked into a rigid piece (the rigid piece 61 temporarily interlocking the extension 33 from pedicle screws of the upper vertebra and the upper lateral plate component 63 extending from the interbody component 60, and rigid piece 62 temporarily interlocking the extension 33 from pedicle screws of the lower vertebra and the lower lateral plate component 64 extending from the interbody component 60) that holds the relative relationship between the components. The rigid piece could be a single solid piece with holes to accept the extensions, or could be a jig that has an adjustment mechanism to allow the user to select different spacing to suit prostheses of different sizes.

Figure 11:
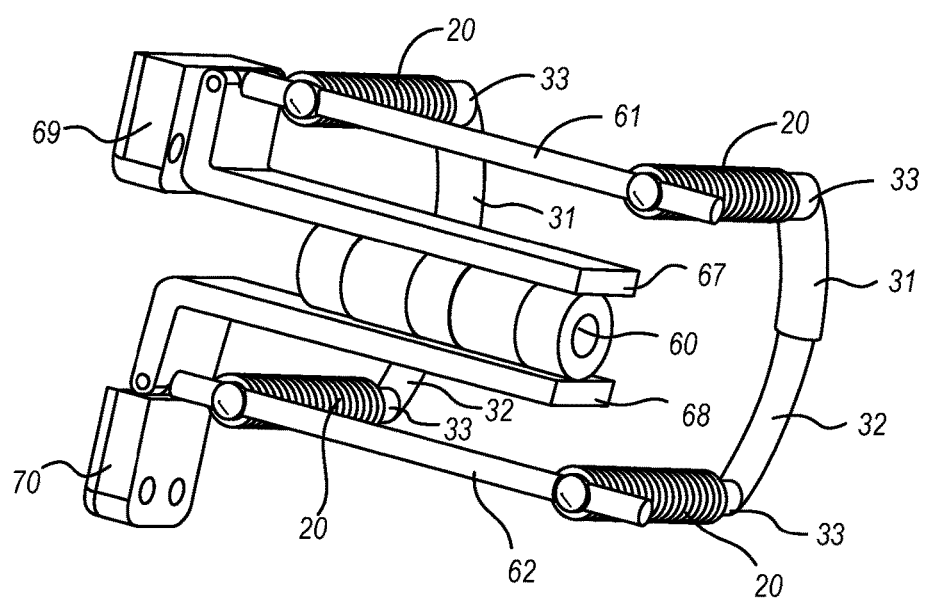
FIG. 11 is a perspective view of still another implementation of a dynamic lumbar spine stabilization device. Pedicle screw extensions and interbody hinge extensions are interconnected by a jig that rotates and has an adjustment mechanism to allow the user to select different spacing to suit interbody prostheses of different sizes.

Various design considerations may be chosen for the interbody component and/or other components. For example, the bilateral anterolateral plate components may exist in different configurations (67, 68 in FIG. 11) and the pieces holding the extensions and plates (69, 70 in FIG. 11) may be rotatable (e.g. hinged).

It may be difficult to align the posterior curved rails with the laterally inserted interbody hinge and plates freehand. However, since the patient is positioned lying on their side during the XLIF procedure, it is possible to temporarily interconnect extensions from the pedicle screws to an alignment jig used during lateral insertion of the interbody prosthesis. The alignment jig would have geometrical constraints forcing a known relationship between the interbody device and pedicle screws. That is, the extension from pedicle screws and an extension from the interbody component would be temporarily locked into a rigid piece that holds the relative relationship between the components. The rigid piece could be a single solid piece with holes to accept the extensions, or could be a jig that has an adjustment mechanism to allow the user to select different spacing to suit prostheses of different sizes. Steps for such a surgical procedure could be: 1). Insert pedicle screws (percutaneously or open) with posterior extension rods, 2). Perform XLIF exposure, prepare disc space, and attach interbody prosthesis insertion tool, 3). Temporarily interconnect posterior extension rods to interbody prosthesis insertion tool with alignment jig, 4). Insert interbody prosthesis, fasten to pedicle screws, and augment with additional bone screws if desired, 5). Detach alignment jig and posterior pedicle screw extension rods, 6). Attach posterior curved rail members to the pedicle screws.

The above steps could obviously be performed in a different order with different design considerations. For example, the posterior curved rail members could be attached to the pedicle screws as the 2nd step instead of the 6th step by designing a fitting on the curved rail member to which posterior pedicle screw extensions rods are secured temporarily. Then the alignment jig would be used to insert the interbody component after posterior curved rails are attached.

It will be understood that implementations are not limited to the specific components disclosed herein, as virtually any components consistent with the intended operation of a dynamic lumbar spine stabilization device implementation may be utilized. Accordingly, for example, although particular components and so forth, are disclosed, such components may comprise any shape, size, style, type, model, version, class, grade, measurement, concentration, material, weight, quantity, and/or the like consistent with the intended operation of a dynamic lumbar spine stabilization device implementation. Implementations are not limited to uses of any specific components, provided that the components selected are consistent with the intended operation of a dynamic lumbar spine stabilization device implementation.

Accordingly, the components defining any dynamic lumbar spine stabilization device implementation may be formed of any of many different types of materials or combinations thereof that can readily be formed into shaped objects provided that the components selected are consistent with the intended operation of a dynamic lumbar spine stabilization device implementation. For example, the components may be formed of: rubbers (synthetic and/or natural) and/or other like materials; ceramics and/or other like materials; polymers such as thermoplastics (such as ABS, Fluoropolymers, Polyacetal, Polyamide; Polycarbonate, Polyethylene, Polyether ether ketone (PEEK), Polysulfone, and/or the like), thermosets (such as Epoxy, Phenolic Resin, Polyimide, Polyurethane, Silicone, and/or the like), any combination thereof, and/or other like materials; composites and/or other like materials; metals, such as zinc, magnesium, titanium, copper, iron, steel, carbon steel, alloy steel, tool steel, stainless steel, spring steel, aluminum, any combination thereof, and/or other like materials; alloys, such as aluminum alloy, titanium alloy, magnesium alloy, copper alloy, cobalt-chromium alloy, any combination thereof, and/or other like materials; any other suitable material; and/or any combination thereof.

For the exemplary purposes of this disclosure, components of dynamic spine stabilization implementations may be made of any material such as polymers, metals, composites, ceramics, and/or the like. The material(s) may be picked so as to make the components have any desirable attribute such as strength, lightweight, durability, and so forth. In one implementation, the curved rail members may be constructed from biocompatible materials such as metal-on-polymer (e.g. polyethylene). In other implementations of dynamic lumbar spine stabilization device, other low-wear biomaterials such as ceramic, polycarbonate, or PEEK may form an articulating layer—flange or coating—at the interface of the curved sleeve, corresponding curved rail moveable within the curved sleeve of each of the curved rail members.

Various dynamic lumbar spine stabilization device implementations may be manufactured using conventional procedures as added to and improved upon through the procedures described here. Some components defining dynamic lumbar spine stabilization device implementations may be manufactured simultaneously and integrally joined with one another, while other components may be purchased pre-manufactured or manufactured separately and then assembled with the integral components.

Manufacture of these components separately or simultaneously may involve extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled with one another in any manner, such as with adhesive, a weld, a fastener (e.g. a bolt, a nut, a screw, a nail, a rivet, a pin, and/or the like), wiring, any combination thereof, and/or the like for example, depending on, among other considerations, the particular material forming the components.

It will be understood that the assembly of dynamic lumbar spine stabilization device implementations are not limited to the specific order of steps as disclosed in this document. Any steps or sequence of steps of the assembly of dynamic lumbar spine stabilization device implementations indicated herein are given as examples of possible steps or sequence of steps and not as limitations, since various assembly processes and sequences of steps may be used to assemble dynamic lumbar spine stabilization device implementations.

In places where the description above refers to particular implementations, it should be readily apparent that a number of modifications may be made without departing from the spirit thereof and that these implementations may be alternatively applied. The accompanying CLAIMS are intended to cover such modifications as would fall within the true spirit and scope of the disclosure set forth in this document. The presently disclosed implementations are, therefore, to be considered in all respects as illustrative and not restrictive, the scope of the disclosure being indicated by the appended CLAIMS rather than the foregoing DESCRIPTION. All changes that come within the meaning of and range of equivalency of the CLAIMS are intended to be embraced therein.

The invention claimed is:

1. A dynamic lumbar spine stabilization device that allows dynamic fixation of both anterior and posterior vertebral columns simultaneously by facilitating partial flexion and extension or up to full normal flexion and extension while stabilizing at least one upper vertebra and at least one lower vertebra of the lumbar spine, wherein the at least one upper vertebra and the at least one lower vertebra are adjacent or non-adjacent, the dynamic lumbar spine stabilization device comprising:

at least four through-shafts, a first through-shaft extending into a right side of the at least one upper vertebra at least up to a location within the vertebra suitable for insertion of pedicle screws, a second through-shaft extending into a left side of the at least one upper vertebra at least up to a location within the vertebra suitable for insertion of pedicle screws, a third through-shaft extending into a right side of the at least one lower vertebra at least up to a location within the vertebra suitable for insertion of pedicle screws, a fourth through-shaft extending into a left side of the at least one lower vertebra at least up to a location within the vertebra suitable for insertion of pedicle screws; and at least two curved rail members, each curved rail member comprising a curved sleeve and a corresponding curved rail moveable within the curved sleeve, the at least two curved rail members coupled to the at least four through-shafts on one of an anterior face, a posterior face, and both anterior and posterior faces of the at least one upper vertebra and the at least one lower vertebra.

2. The device of claim 1 wherein the device allows free movement in a sagittal plane while allowing minimum axial rotation and lateral bending.

3. The device of claim 2 wherein the first and the second through-shafts and the third and the fourth through-shafts extend all the way through the at least one upper vertebra and the at least one lower vertebra, respectively, from an anterior face to a posterior face, and wherein the at least two curved rail members comprise first, second, third, and fourth curved rail members, the first curved rail member coupled to the first and the third through-shafts on the posterior face, the second curved rail member coupled to the second and the fourth through-shafts on the posterior face, the third curved rail member coupled to the first and the third through-shafts on the anterior face, and the fourth curved rail member coupled to the second and the fourth through-shafts on the anterior face.

4. The device of claim 2 wherein, for each of the at least two curved rail members, the curved sleeve and the corresponding curved rail moveable within the curved sleeve is curved in a circular path with a path of curvature oriented in a sagittal plane, and wherein, for each of the at least two curved rail members, the curved sleeve and the corresponding curved rail moveable within the curved sleeve extends all the way through a space between the at least one upper vertebra and the at least one lower vertebra or extend partially through a space between the at least one upper vertebra and the at least one lower vertebra.

5. The device of claim 2 wherein the at least four through-shafts are selected from the group consisting of solid screws, non-threaded shafts, hollow shafts with cores, or hollow shafts with inserts.

6. The device of claim 2 further comprising a protective sheath to prevent tissue ingrowth over an area where the curved sleeve and the corresponding curved rail moveable within the curved sleeve of each of the at least two curved rail members slide.

7. The device of claim 2 wherein the at least two curved rail members are coupled to the at least four through-shafts at one or more places by at least one shaft extension to allow adjustment of an anteroposterior position of the curved sleeve and the corresponding curved rail moveable within the curved sleeve of each of the two curved rail members in situ.

8. The device of claim 2 further comprising rigid pieces between the at least two curved rail members on left and right sides of the at least one upper vertebra and the at least one lower vertebra on one of an anterior face or a posterior face or both anterior and posterior faces to provide additional resistance to lateral bending and axial rotation.

9. The device of claim 2 further comprising wings that are deployed laterally after the at least four through-shafts have been placed to enhance a horizontal surface area covered by the at least four through-shafts thereby preventing vertical migration of the at least four through-shafts through a vertebral body of each of the at least one upper vertebra and the at least one lower vertebra in conditions such as osteoporosis.

10. The device of claim 2 further comprising a low-wear biomaterial flange or coating to create metal-on-low-wear biomaterial interface between the curved sleeve and the corresponding curved rail moveable within the curved sleeve of each of the at least two curved rail members, wherein the metal-on-low-wear biomaterial produces low-wear debris and is selected from the group consisting of ceramic, polycarbonate, polyethylene, polyether ether ketone, or any low-wear biocompatible polymer.

11. The device of claim 2 further comprising elastic bumpers or dashpots or both bumpers and dashpots at ends of the curved sleeve or the corresponding curved rail moveable within the curved sleeve of each of the at least two curved rail members to prevent stiff abrupt stops when the end of the corresponding curved rail moveable within the curved sleeve collides with the end of the curved sleeve thereby controlling magnitude and speed of rotation of the at least two curved rail members.

12. The device of claim 2 further comprising springs at ends of the curved sleeve or the corresponding curved rail moveable within the curved sleeve of each of the at least two curved rail members to allow controlling position of a joint to a desired neutral position and to provide elastic resistance to motion away from the desired neutral position.

13. The device of claim 2 wherein the curved sleeve and the corresponding curved rail moveable within the curved sleeve of each of the at least two curved rail members have a non-circular cross-section.

14. A modified dynamic lumbar spine stabilization device that allows dynamic fixation of both anterior and posterior vertebral columns simultaneously by facilitating partial flexion and extension or up to full normal flexion and extension and also provides additional support against compression while stabilizing at least one upper vertebra and at least one lower vertebra of the lumbar spine, wherein the at least one upper vertebra and at least one lower vertebra of the lumbar spine are adjacent, the modified dynamic lumbar spine stabilization device comprising:

at least four through-shafts, a first through-shaft extending into a right side of the at least one upper vertebra at least up to a location within the vertebra suitable for insertion of pedicle screws, a second through-shaft extending into a left side of the at least one upper vertebra at least up to a location within the vertebra suitable for insertion of pedicle screws, a third through-shaft extending into a right side of the at least one lower vertebra at least up to a location within the vertebra suitable for insertion of pedicle screws, and a fourth through-shaft extending into a left side of the at least one lower vertebra at least up to a location within the vertebra suitable for insertion of pedicle screws, or at least four pedicle screws, a first pedicle screw inserted into a right side of the at least one upper vertebra, a second pedicle screw inserted into a left side of the at least one upper vertebra, a third pedicle screw inserted into a right side of the at least one lower vertebra, and a fourth pedicle screw inserted into a left side of the at least one lower vertebra;

at least two curved rail members, each curved rail member comprising a curved sleeve and a corresponding curved rail moveable within the curved sleeve, the at least two curved rail members comprising first and second curved rail members, the first curved rail member coupled to the first and the third through-shafts, or the first and the third pedicle screws, on a posterior face of the at least one upper vertebra and the at least one lower vertebra of the lumbar spine, and the second curved rail member coupled to the second and the fourth through-shafts, or the second and the fourth pedicle screws on a posterior face of the at least one upper vertebra and the at least one lower vertebra of the lumbar spine; and at least one interbody component placed in an intervertebral disc space of the at least one upper vertebra and the at least one lower vertebra for providing additional support against compression, an upper half of the at least one interbody component rigidly interconnected to the first and the second through-shafts, or the first and the second pedicle screws and to upper halves of the first and the second curved rail members, a lower half of the at least one interbody component rigidly interconnected to the third and the fourth through-shafts, or the first and the fourth pedicle screws and to lower halves of the first and the second curved rail members, the upper and the lower halves of the at least one interbody component sharing a common axis of rotation with the at least two curved rail members.

15. The device of claim 14, wherein the at least one interbody component is selected from the group consisting of ball and socket, a cylindrical hinge with axis perpendicular to a sagittal plane, a flexible and pliable material with mechanical properties of soft rubber, or any other biocompatible elastomeric material that allows free flexion and extension.

16. The device of claim 14 further comprising plates and at least one of bone screws and cement to secure the at least one interbody component to vertebral bodies of the at least one upper vertebra and the at least one lower vertebra.

17. The device of claim 16 wherein the plates comprise attachment plates interconnecting the at least one interbody component and the at least two curved rail members to facilitate the at least one interbody component and the at least two curved rail members share a desired common axis of rotation.

18. The device of claim 16 wherein the plates comprise left, right or bilateral anterolateral plate components extending from the at least one interbody component to secure the at least one interbody component to vertebral bodies of the at least one upper vertebra and the at least one lower vertebra.

19. The device of claim 14, wherein the first and the second through-shafts and the third and the fourth through-shafts extend all the way through the at least one upper vertebra and the at least one lower vertebra, respectively, from an anterior face to a posterior face, wherein the at least two curved rail members comprise of first, second, third, and fourth curved rail members, the first curved rail member coupled to the first and the third through-shafts on the posterior face, the second curved rail member coupled to the second and the fourth through-shafts on the posterior face, the third curved rail member coupled to the first and the third through-shafts on the anterior face, and the fourth curved rail member coupled to the second and the fourth through-shafts on the anterior face, wherein the upper half of the at least one interbody component is rigidly interconnected to the first and the second through-shafts and upper halves of the first and the second curved rail members and the lower half of the at least one interbody component is rigidly interconnected to the third and the fourth through-shafts and to lower halves of the first and the second curved rail members, or the upper half of the at least one interbody component is rigidly interconnected to the first and the second through-shafts and upper halves of the third and the fourth curved rail members and the lower half of the at least one interbody component is rigidly interconnected to the third and the fourth through-shafts and to lower halves of the third and the fourth curved rail members, and wherein the first, the second, the third and the fourth through-shafts, the first, the second, the third and the fourth curved rail members, the at least one interbody component, and other components of the device are surgically implanted into a subject by both an anterior exposure and a posterior exposure.

\* \* \* \* \*